(12) United States Patent
Kemp et al.

(10) Patent No.: US 9,061,103 B2
(45) Date of Patent: Jun. 23, 2015

(54) AUTO-INJECTOR

(75) Inventors: Thomas Kemp, Hertfordshire (GB);
Douglas Jennings, Herts (GB);
Matthew Ekman, Cheshire (GB)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 0 days.

(21) Appl. No.: 13/994,890

(22) PCT Filed: Dec. 21, 2011

(86) PCT No.: PCT/EP2011/073514
§ 371 (c)(1),
(2), (4) Date: Jun. 17, 2013

(87) PCT Pub. No.: WO2012/085032
PCT Pub. Date: Jun. 28, 2012

(65) Prior Publication Data
US 2013/0281936 A1     Oct. 24, 2013

Related U.S. Application Data
(60) Provisional application No. 61/432,235, filed on Jan. 13, 2011.

(30) Foreign Application Priority Data
Dec. 21, 2010 (EP) .................................... 10196078

(51) Int. Cl.
*A61M 5/28* (2006.01)
*A61M 5/24* (2006.01)
*A61M 5/00* (2006.01)
*A61M 5/20* (2006.01)
*A61M 5/32* (2006.01)
*A61M 5/46* (2006.01)

(52) U.S. Cl.
CPC . *A61M 5/28* (2013.01); *A61M 5/24* (2013.01);
*A61M 2005/2414* (2013.01); *A61M 5/002*
(2013.01); *A61M 5/2033* (2013.01);
(Continued)

(58) Field of Classification Search
CPC ............. A61M 2005/2414; A61M 2005/3152;
A61M 5/002; A61M 5/2033; A61M 5/24;
A61M 5/28; A61M 5/326; A61M 5/46;
A61M 2005/202; A61M 2005/2403
USPC .................. 604/197, 198, 134–138, 156, 157
See application file for complete search history.

(56) References Cited

U.S. PATENT DOCUMENTS 4,300,554 A * 11/1981 Hessberg et al. ............. 604/135
6,159,161 A * 12/2000 Hodosh ......................... 600/561
(Continued)

FOREIGN PATENT DOCUMENTS

WO     2010/018411     2/2010
WO     2010/076569     7/2010

OTHER PUBLICATIONS

International Search Report for Int. App. No. PCT/EP2011/073514, completed Apr. 20, 2012.

*Primary Examiner* — Kami A Bosworth
(74) *Attorney, Agent, or Firm* — McDonnell Boehnen Hulbert & Berghoff LLP

(57) ABSTRACT

An auto-injector for delivering a liquid medicament (M) is presented having an elongate housing having a loading bay configured to receive a packaged syringe, wherein the loading bay is configured to be laterally accessible for inserting or removing the packaged syringe, wherein a sliding door is slidably arranged over the housing in a manner to reveal the loading bay in a distal position and to cover the loading bay in a proximal position.

12 Claims, 13 Drawing Sheets

(52) U.S. Cl.
CPC ................ *A61M 5/326* (2013.01); *A61M 5/46* (2013.01); *A61M 2005/202* (2013.01)

(56) References Cited

U.S. PATENT DOCUMENTS

| | | |
|---|---|---|
| 6,599,272 B1 * | 7/2003 | Hjertman et al. ............ 604/209 |
| 7,678,084 B2 * | 3/2010 | Judson et al. ................ 604/187 |
| 2002/0095120 A1 | 7/2002 | Larsen et al. |
| 2005/0273055 A1 | 12/2005 | Harrison et al. |
| 2010/0137832 A1 * | 6/2010 | Mathews et al. ............. 604/506 |
| 2011/0033832 A1 * | 2/2011 | Baba et al. .................... 434/262 |
| 2012/0172815 A1 * | 7/2012 | Holmqvist .................... 604/208 |
| 2012/0279329 A1 * | 11/2012 | Veasey et al. ..................... 74/34 |

\* cited by examiner

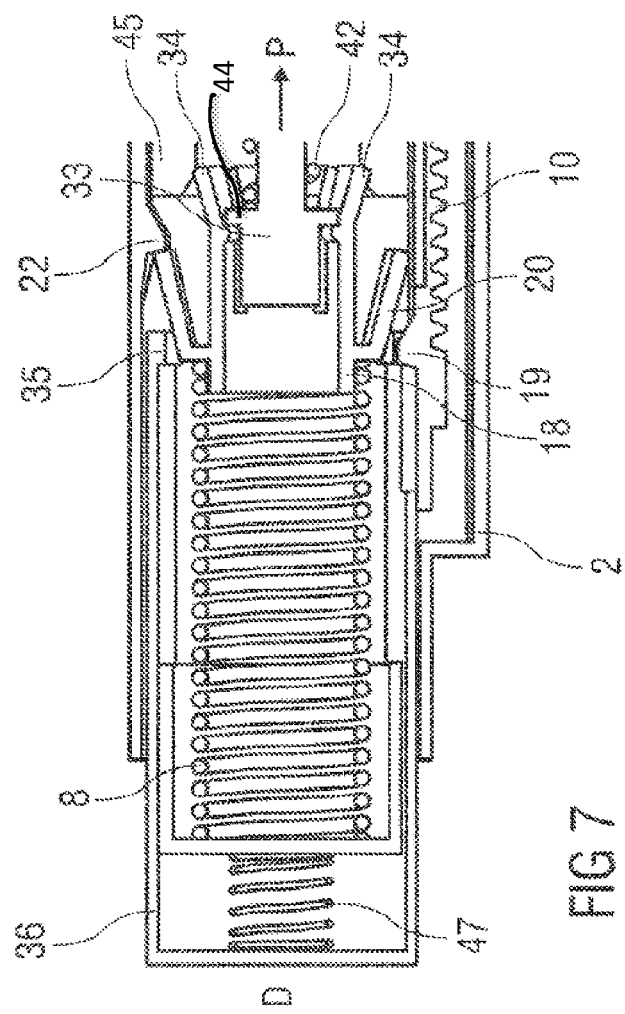

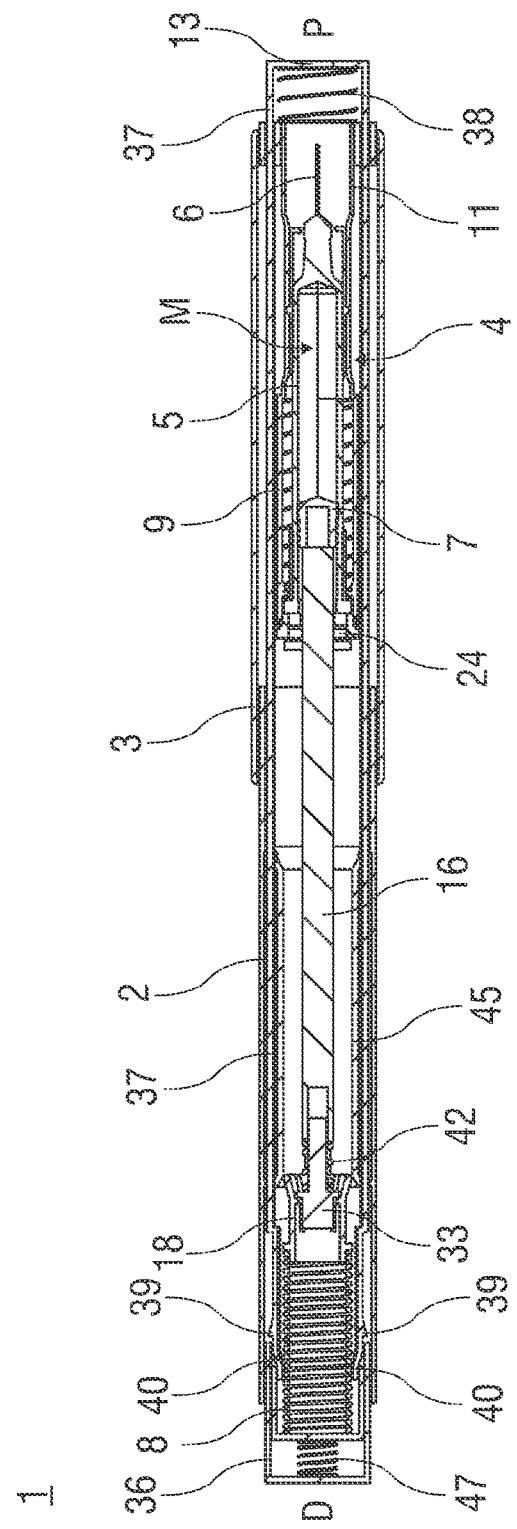

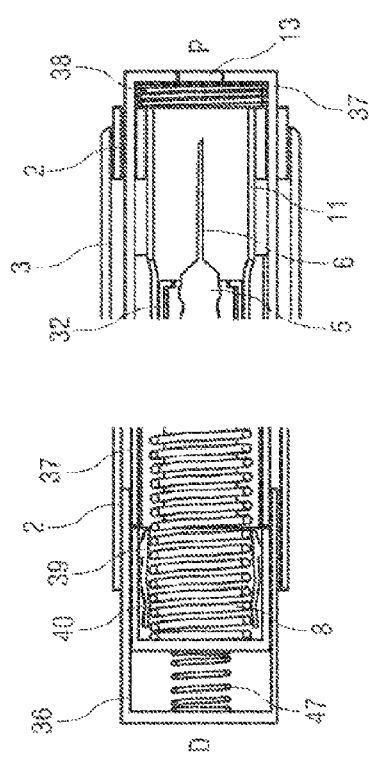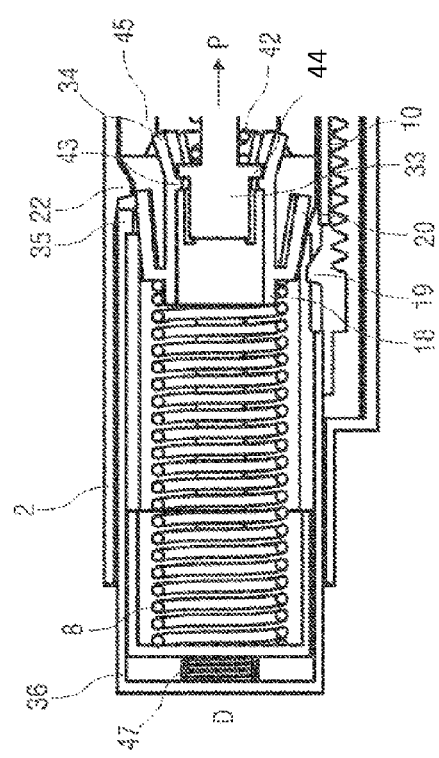

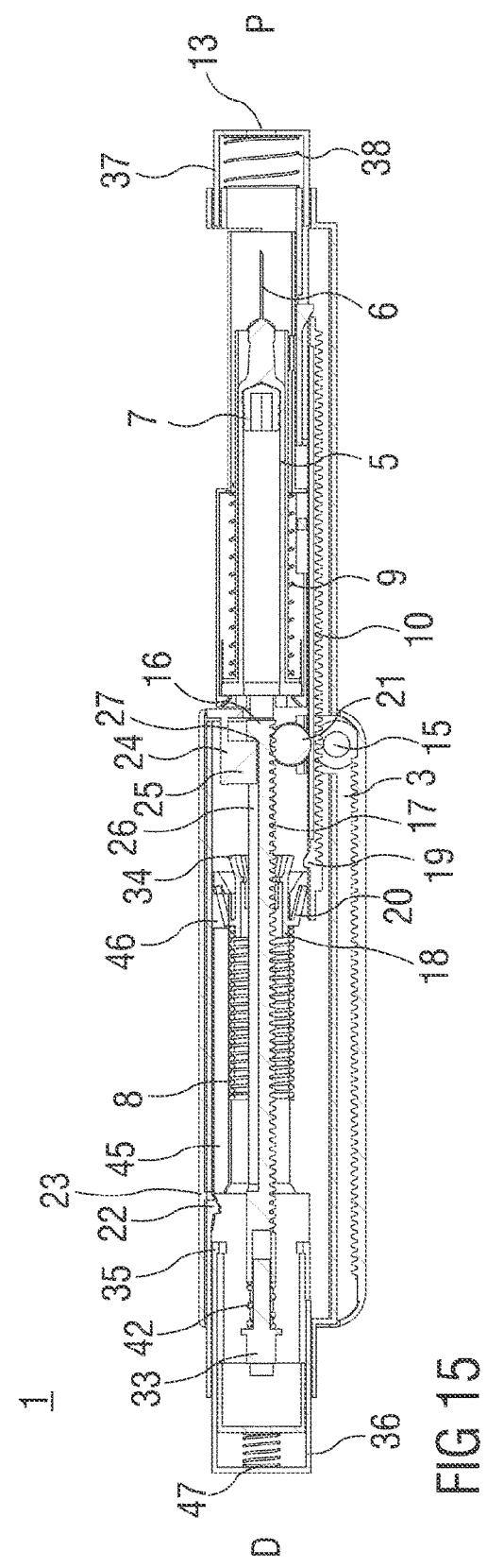

AUTO-INJECTOR

CROSS REFERENCE TO RELATED APPLICATIONS

The present application is a U.S. National Phase Application pursuant to 35 U.S.C. §371 of International Application No. PCT/EP2011/073514 filed Dec. 12, 2011, which claims priority to European Patent Application No. 10196078.9 filed Dec. 21, 2010 and U.S. Provisional Patent Application No. 61/432,235 filed Jan. 13, 2011. The entire disclosure contents of these applications are herewith incorporated by reference into the present application.

TECHNICAL FIELD

The invention relates to an auto-injector for administering a dose of a liquid medicament according to the preamble of claim 1.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification the term proximal refers to the direction pointing towards the patient during an injection while the term distal refers to the opposite direction pointing away from the patient.

An auto-injector for delivering a liquid medicament according to the invention comprises an elongate housing having a loading bay configured to receive a packaged syringe, wherein the loading bay is configured to be laterally accessible for inserting or removing the packaged syringe, wherein a sliding door is slidably arranged over the housing in a manner to reveal the loading bay in a distal position and to cover the loading bay in a proximal position.

The packaged syringe may comprise a syringe with a hollow injection needle and a stopper for sealing the syringe and displacing the liquid medicament. A drive spring is arranged in the housing for advancing the syringe and the needle in proximal direction for needle insertion into an injection site and for injecting the medicament through the needle. The sliding door may exhibit a door rack gear in mesh with a drive gear which is also in mesh with a drive reset rack such that the sliding door and the drive reset rack translate in opposite directions, wherein the drive reset rack is arranged to compress the drive spring on translation in distal direction.

When a new packaged syringe has been loaded into the loading bay a user translates the sliding door into the proximal position thereby translating the drive reset rack in distal direction and resetting the drive spring. Conventional re-usable auto-injectors are reset prior to the loading and are in a primed state when an unused syringe is loaded. The advantage of resetting the auto-injector after the syringe has been loaded is that the user is less likely to incur an injury as they load an unused syringe.

The auto-injector is reset by translating the sliding door along the longitudinal axis of the auto-injector. The sliding door does preferably not protrude beyond either end of the auto-injector regardless of its position within the reset motion. Conventional re-usable auto-injectors are reset by translating a part along their longitudinal axis, but the part frequently extends beyond the ends of the auto-injector. If the auto-injector is released by the user before having been fully reset the part quickly returning into its extending position may cause uncontrolled motion of the auto-injector. The advantage of the sliding door not protruding beyond the auto-injector length is that releasing the auto-injector prior to complete resetting will not result in a projectile and hence the user is less likely to incur an injury as they reset the auto-injector.

The compression drive spring that provides the axial motion for needle insertion and emptying of the syringe is reset by translation of the sliding door. The motion of the sliding door is coupled to the compression spring through two rack and pinion gear pairs, i.e. the door rack gear to the drive gear and the drive gear to the drive reset rack. By using a different number of teeth on two pinion gears, the translating force can be increased by the ratio of the number of gear teeth. This has the advantage of reducing the user effort required to reset the auto-injector.

A plunger may be arranged for transferring load from the drive spring to the syringe and/or to the stopper, wherein the plunger comprises a plunger rack gear, wherein a plunger gear is in mesh with the drive gear and the plunger rack gear in such a manner that the plunger translates in distal direction on translation of the sliding door in distal direction wherein a sprag clutch allows translation of the plunger in proximal direction without interference with the sliding door. The sprag clutch may be arranged in the plunger gear. As the plunger is translated into the syringe for injection it has to be re-translated out of the syringe in order to be able to remove the used syringe post injection. The engagement to the sliding door causes the plunger to translate in distal direction out of the syringe when the sliding door is moved into the distal position for revealing the loading bay. The sprag clutch ensures that the plunger can be advanced for needle insertion and injection without interfering with the sliding door.

The drive spring may be distally grounded in the housing and proximally bearing against a drive collar arranged to be engaged by the drive reset rack for compression of the drive spring. The drive collar is arranged to be latched to the housing when reaching a reset position during compression so as to prevent release of the drive spring from the reset position. An activating means such as a trigger button is arranged to de-latch the drive collar from the housing for starting an injection cycle.

The trigger button may be arranged at a distal end of the housing biased in distal direction so as to protrude from the housing and arranged for de-latching the drive collar from the housing on depression in order to release the drive spring. Alternatively the trigger button may be arranged laterally or in the shape of wrap-over sleeve button extending over a substantial length of the auto-injector.

A plunger shuttle may be slidably arranged in the housing, the plunger shuttle having a boss arranged to abut against a proximal stop on the plunger on translation of the plunger shuttle in proximal direction, wherein a rib on the sliding door is arranged to abut against the plunger shuttle on translation of the sliding door in proximal direction. The plunger shuttle is arranged to abut against the packaged syringe on translation in proximal direction in such a manner that near the end of translation of the sliding door into the proximal position the sliding door translates the plunger shuttle, the plunger shuttle translates the packaged syringe into an actuate position and the plunger shuttle translates the plunger in such a manner that a distal head of the plunger passes through the drive collar and is latched to the drive collar for coupling the drive spring to the plunger.

The packaged syringe may comprise a package housing with the syringe slidably arranged in the package housing. At least one resilient snap arm in the package housing may be arranged to prevent translation of the syringe relative to the package housing for preventing inadvertent exposure of the needle during handling of the packaged syringe. The plunger shuttle may comprise at least one ramp arranged to deflect the snap arm for releasing the syringe on further translation of the plunger shuttle when the packaged syringe is in the actuate position. Thus the syringe and needle are only released for needle insertion when the sliding door has been closed and the auto-injector is ready to fire.

A skin contact interlock sleeve may be slidably telescoped in the housing and biased in proximal direction so as to protrude from the proximal end of the housing in a proximal position, wherein the skin contact interlock sleeve is arranged to interact with the trigger button in a manner to prevent depression of the trigger button when the skin contact interlock sleeve is in the proximal position, i.e. not pressed against the injection site and wherein the skin contact interlock sleeve is arranged to disengage from the trigger button on depression of the interlock sleeve in the distal direction, i.e. on contact to the injection site thus allowing depression of the trigger button. Hence, the user is required to perform a sequence of operations in order to trigger the injection cycle thus reducing the risk of inadvertent triggering.

A retraction spring may be arranged in the packaged syringe in a manner to be compressed on translation of the syringe for needle insertion and to retract the syringe and the needle on de-latching of the distal head from the drive collar.

Hence, once the trigger button has been pressed the auto-injector will insert the needle, fully empty the syringe and then retract the needle to a safe position with no user intervention.

The housing may comprise a reduced diameter section arranged to prevent de-latching of the drive collar from the distal head of the plunger when the drive collar is between the reset position and a decoupling position where the stopper has at least nearly bottomed out in the syringe. As the drive spring keeps pushing the drive collar while the stopper and plunger have bottomed out the distal head de-latches from the drive collar in a manner to allow it to translate in distal direction out of the syringe independently from the drive collar. The plunger will be translated out of the syringe on translation of the sliding door into the distal position as described above.

Reliably triggering the retraction of the syringe and needle at the end of an injection normally has to be traded off against an incompletely emptied syringe, which is undesirable. Due to manufacturing tolerances of the syringe and stopper the exact position of the stopper at the end of its travel is not repeatable. Consequently, in some cases the stopper will prematurely bottom out so the retraction will not be triggered at all. In other cases the retraction will be triggered before the stopper bottomed out so residual medicament remains in the syringe.

This problem may be addressed by releasing the retraction sleeve from the housing a certain amount of time or travel before the stopper bottoms out in the syringe.

For this purpose the distal head may be telescoped with the plunger and biased against the plunger by a plunger spring. As the plunger is advanced for injection the plunger spring is compressed.

A viscous damper may be arranged for being contacted by the drive collar on translation of the drive collar during injection just before the stopper bottoms out in the syringe. The viscous damper is arranged to slow down the speed of the drive collar allowing the plunger spring to extend and translate the stopper until it bottoms out. The position of the viscous damper is selected relative to the reduced diameter section in a manner to allow de-latching of the distal head from the drive collar shortly before the viscous damper is fully compressed by the drive collar.

Thus both problems are solved, reliably retracting the needle to a safe position and fully emptying the syringe which is particularly desirable with expensive drugs. Emptying the syringe is also important for dosage accuracy.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 7 is a distal end of the auto-injector with the drive collar being driven in proximal direction, FIG. 8 is another longitudinal section of the auto-injector of FIG. 5 in a different section plane, FIG. 9 shows details of the distal end and the proximal end of the auto-injector during skin contact of the proximal end, FIG. 10 is the distal end with the trigger button being depressed, FIG. 15 is the auto-injector during removal of the packaged syringe after injection.

Corresponding parts are marked with the same reference symbols in all figures.

DETAILED DESCRIPTION

Figure 1:
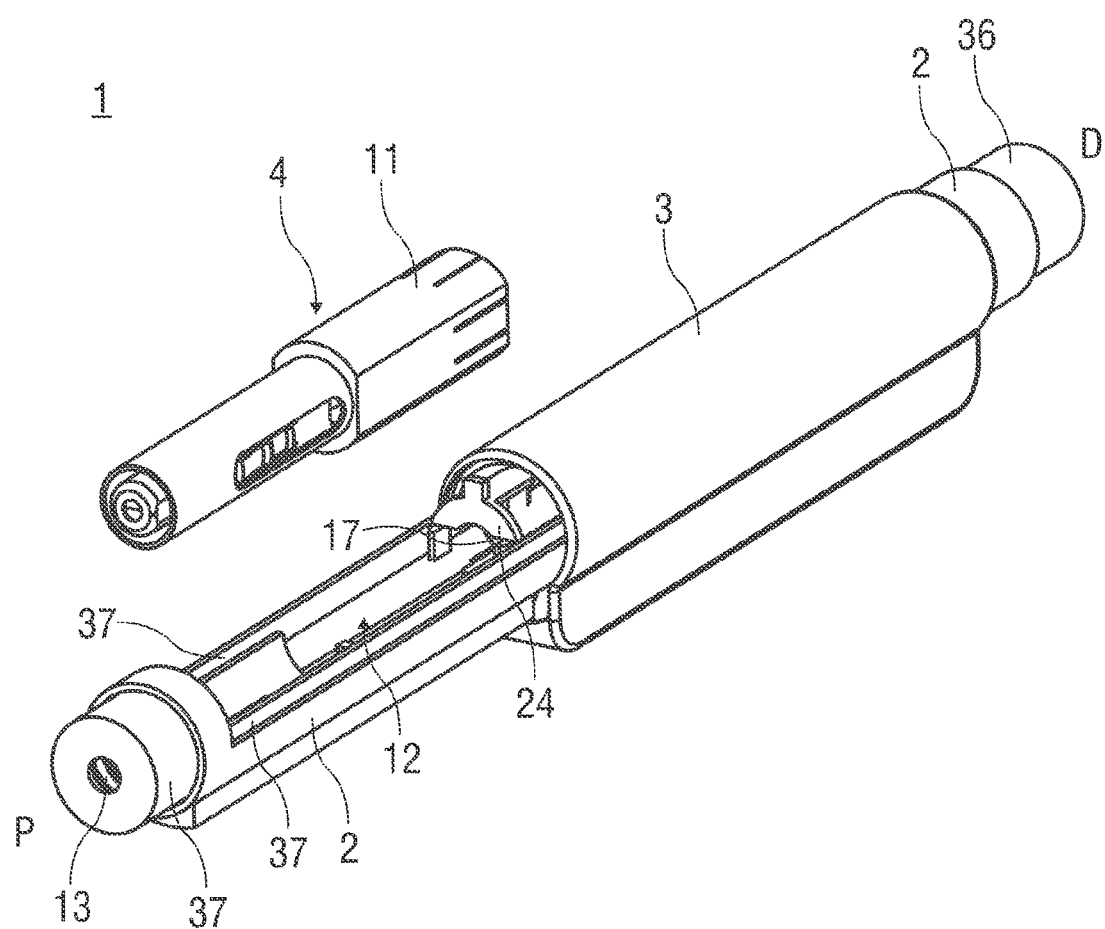
FIG. 1 is an isometric view of a reusable auto-injector with sliding door loading during insertion of a packaged syringe.

FIG. 1 shows an isometric view of a reusable auto-injector with sliding door loading during insertion of a packaged syringe. The auto-injector 1 comprises an elongate housing 2 and a sliding door 3 which may be axially translated by a user in order to reveal a loading bay 12 into which a disposable packaged syringe 4 may be inserted. Translation of the sliding door 3 also resets the auto-injector 1 for further operations.

Figure 2:
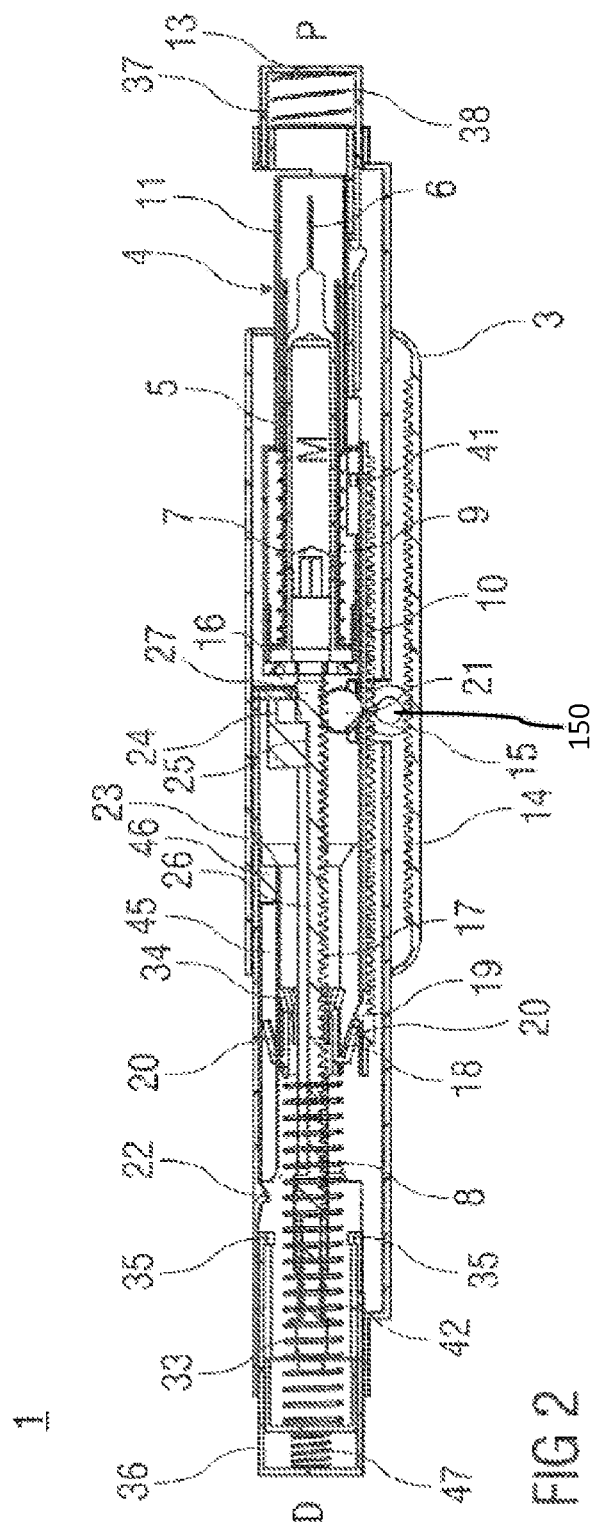
FIG. 2 is the auto-injector during closing of the sliding door.

The packaged syringe 4 comprises a syringe 5 with a hollow injection needle 6 and a stopper 7 for sealing the syringe 5 and displacing a liquid medicament M for injection (see FIG. 2 for details). The packaged syringe 4 shown in the embodiments further comprises a package housing 11 surrounding the syringe 5 and arranged to allow relative axial translation between the syringe 5 and the syringe housing 11. The needle 6 is equipped with a protective needle sheath (not illustrated) for keeping the needle 6 sterile and preventing it from being mechanically damaged.

Figure 5:
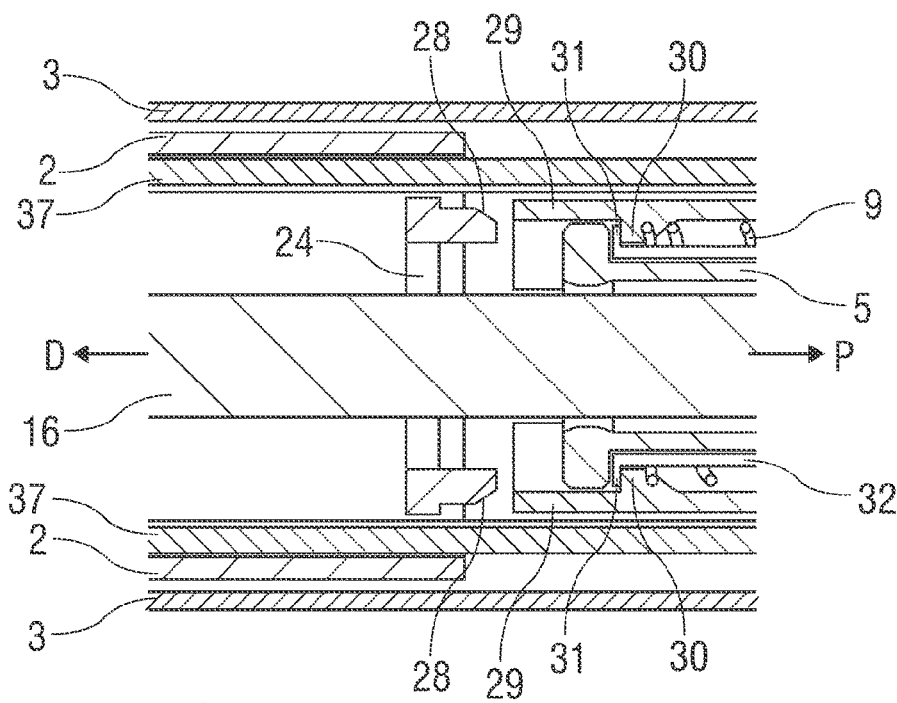
FIG. 5 is a detail view showing a plunger shuttle before contacting the syringe.

At a distal end of the package housing 11 resilient snap arms 29 are arranged (see FIG. 5 for details). An internal stop 30 on each snap arm 29 is arranged to abut against a distal flange 31 on a syringe carrier sleeve 32 in a manner to prevent it from translating in proximal direction P. The syringe carrier sleeve 32 is arranged for holding the syringe 5, i.e. the syringe carrier sleeve 32 and the syringe 5 always translate together.

A drive means 8 in the shape of a compression spring 8 is arranged in a distal part of the housing 2. The drive means 8 is arranged to cause an axial translation for inserting the needle 6 through an orifice 13 at a proximal end P into an injection site, e.g. a patient's skin and for advancing the stopper 7 in proximal direction P for injecting the dose of medicament M. Another compression spring is arranged as a retraction spring 9 for retracting the needle 6 to a safe position after the end of the injection. The retraction spring 9 is part of the packaged syringe 4 in the embodiment shown, however it could equally be part of the reusable auto-injector 1.

The axial motion from the drive means 8 to the packaged syringe 4 or the stopper 7 is transmitted by a plunger 16 having a plunger rack gear 17. A drive collar 18 is arranged around the plunger 16. The drive means 8 is grounded in the distal end of the housing 2 and bearing against the drive collar 18.

A skin contact interlock sleeve 37 is slidably telescoped in the housing 2 and biased in proximal direction P by an interlock spring 38 so as to protrude from the proximal end P of the housing 2. The skin contact interlock sleeve 37 extends almost through the entire housing 2 to the distal end D (see FIG. 8).

A sequence of operation of the auto-injector 1 is as follows:

The sliding door 3 is axially translated in distal direction D in order to reveal the loading bay 12, i.e. an aperture in the housing 2. The user inserts a packaged syringe 4 into the loading bay 12 (see FIG. 1). The protective needle sheath may be removed from the needle prior to insertion of the packaged syringe 4 into the loading bay 12. Likewise the auto-injector 1 could be arranged to allow removal of the protective needle sheath through the orifice 13 after insertion of the packaged syringe 4.

The user translates the sliding door 3 in proximal direction P in order to close the auto-injector 1 (see FIG. 2). A door rack gear 14 on an internal surface of the sliding door 3 meshes with a drive gear 15 pivoted in the housing 2. On an opposite side the drive gear 15 is also in mesh with a drive reset rack 10 arranged inside the housing 2 so the sliding door 3 and the drive reset rack 10 are arranged to travel in opposite directions. Therefore as the sliding door 3 is moved in proximal direction P the drive reset rack 10 moves in distal direction D. Near a distal end of the drive reset rack 10 a catch 19 is arranged which engages an outer latch arm 20 at the drive collar 18 so the drive reset rack 10 travelling in distal direction D takes the drive collar 18 with it and compresses the drive means 8.

A plunger gear 21 is in mesh with the drive gear 15 and the plunger rack gear 17 however a sprag clutch 150 (see FIG. 2) prevents transmission of torque from the drive gear 15 through to the plunger rack gear 17 when the sliding door 3 is being translated in proximal direction P. The drive gear 15 consists of two gears of differing teeth number. One is in mesh with the plunger gear 21 and the other in mesh with the door rack gear 14. The two gears of the drive gear 15 are coupled together by the sprag clutch 150 allowing transmission of torque in one direction only—from the sliding door 3 to the plunger 16.

Figure 3:
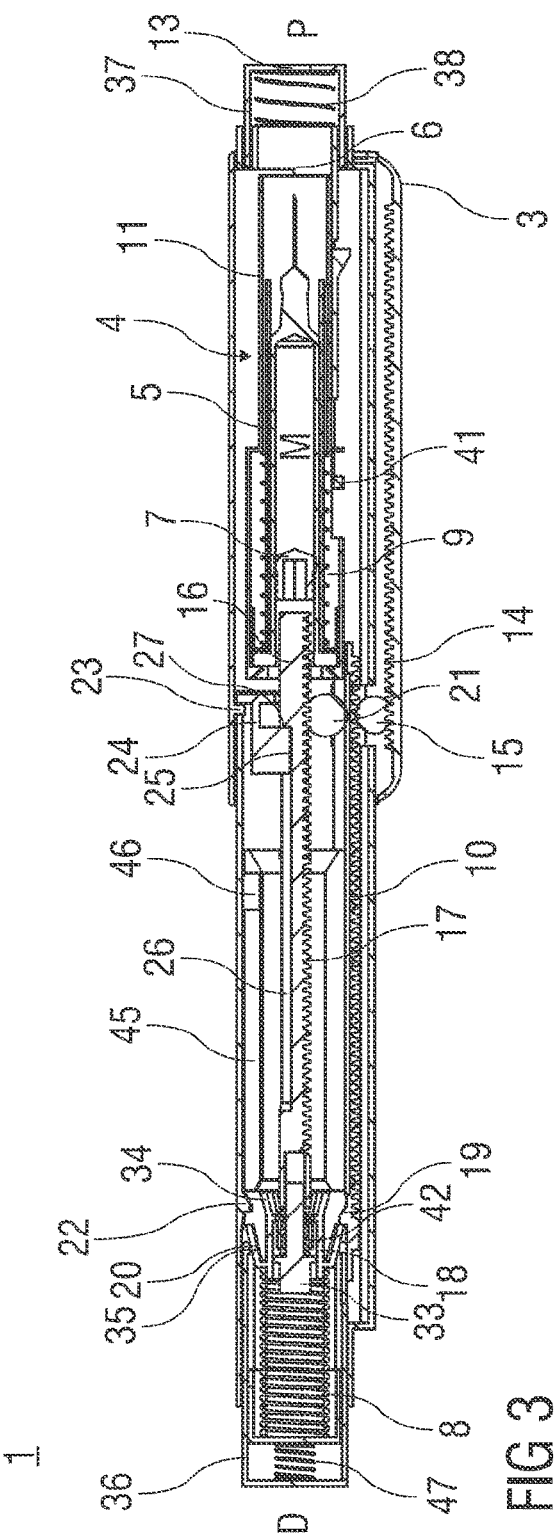
FIG. 3 is the auto-injector with the sliding door almost completely closed and the syringe in a loading position.

When the sliding door 3 is approaching a fully closed position (see FIG. 3), the outer latch arms 20 on the drive collar 18 snap past internal first ribs 22 in the housing 2. If the sliding door 3 is released in this position, the force of the drive means 8 on the drive collar 18 will be resolved through the housing 2. The drive collar 18 is now in a reset position. If the sliding door 3 is released prior to this stage, i.e. before the drive collar 18 has snapped past the internal first ribs 22, the sliding door 3 will be driven open by the drive means 8 and thus does not present a finger trap hazard to the user. As the sliding door 3 approaches the end of travel the outer latch arms 20 are deflected inwards by trigger button arms 35 on a trigger button 36 arranged at the distal end D of the auto-injector 1. The trigger button 36 is biased in distal direction D by a trigger spring 47 bearing against the housing 2 and against the trigger button 36.

Figure 4:
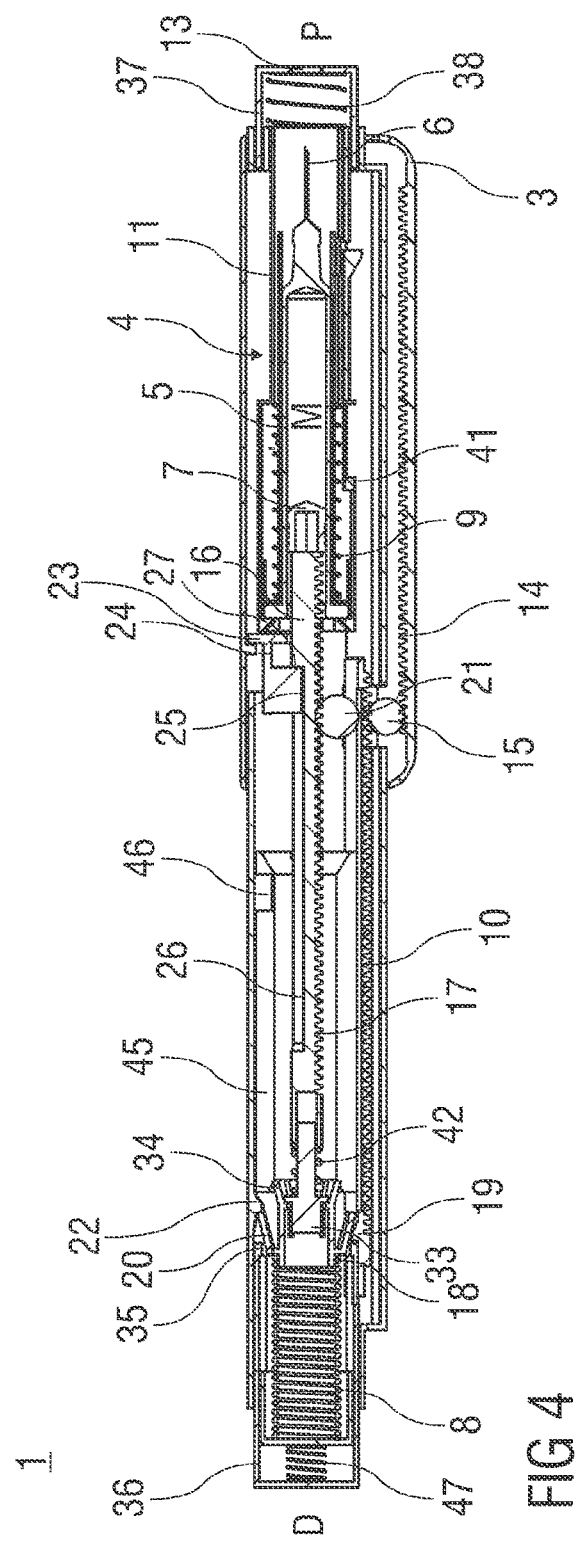
FIG. 4 is the auto-injector with the syringe being translated from the loading position into an actuate position.

On inward deflection the outer latch arms 20 come clear from the catch 19 (see FIG. 4). The drive collar 18, no longer restrained by the catch 19, translates in proximal direction P under load of the drive spring 8 until the outer latch arms 20 abut against the first rib 22 (see FIG. 4) returning into the reset position. The trigger button 36 cannot yet be depressed in this situation due to its trigger button arms 35 abutting against outward stops 39 on the skin contact interlock 37 (see FIG. 8).

Figure 6:
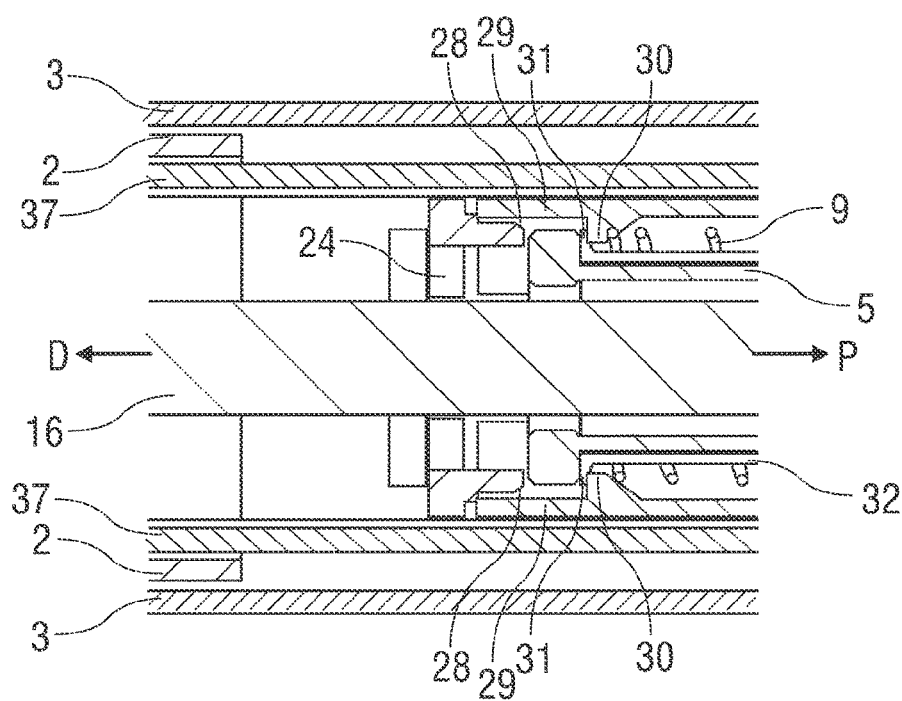
FIG. 6 is a detail view with the plunger shuttle having contacted the syringe.

In parallel, as the sliding door 3 is being closed, a second rib 23 on the sliding door 3 comes into contact with a plunger shuttle 24 taking the plunger shuttle 24 with it in proximal direction P (see FIG. 4). The plunger shuttle 24 contacts the package housing 11 and moves the packaged syringe 4 from the loading bay 12 to an actuate position (see FIG. 4). A boss 25 on the plunger shuttle 24 is engaged within a longitudinal groove 26 in the plunger 16. As the boss 25 abuts against a proximal stop 27 at a proximal end of the groove 26 during the translation the plunger 16 is caused to move with the sliding door 3. The plunger 16 moves towards the stopper 7 reducing the motion required from the drive spring 8 in a later stage. Further movement of the plunger shuttle 24 enables ramps 28 (see FIG. 5) on the plunger shuttle 24 to deflect the snap arms 29 on the package housing 11 outwards. As the snap arms 29 are outwardly deflected the stops 30 in the package housing 11 are also deflected thus releasing the syringe carrier sleeve 32 with the syringe 5 for translation in proximal direction P relative to the package housing 11 (see FIG. 6).

In parallel, a distal head 33 telescoped in the plunger 16 and biased against the plunger 16 by a plunger spring 42 is drawn through the drive collar 18. Inner latch arms 34 on the drive collar 18 are deflected outwards by a shoulder 44 on the distal head 33 and allow the distal head 33 to be pulled through the drive collar 18. This enables the drive force from the drive spring 8 to be transferred to the plunger 16 (see FIG. 7).

With the final motion of closing the sliding door 3, the outer latch arms 20 on the drive collar 18 are driven against the trigger button arms 35 deflecting the outer latch arms 20 inwards for de-latching the drive reset rack 10 from the drive collar 18 (see FIG. 4).

The drive collar 18 is then returned to the reset position with the outer latch arms 20 abutting against the first rib 22 through the force of the drive spring 8. The auto-injector 1 is now fully reset (see FIG. 4).

In order to trigger an injection the user presses the auto-injector 1 against the injection site, e.g. a patient's skin. This causes the skin contact interlock 37 to translate in distal direction D within the housing 2. As the skin contact interlock 37 translates, the outward stops 39 preventing depression of the trigger button 36 are deflected inwards by ramps 40 within the housing 2 allowing depression of the trigger button 36 (see FIG. 9). This feature prevents the user from accidentally actuating the auto-injector 1 when it is not in contact with the injection site.

Figure 11:
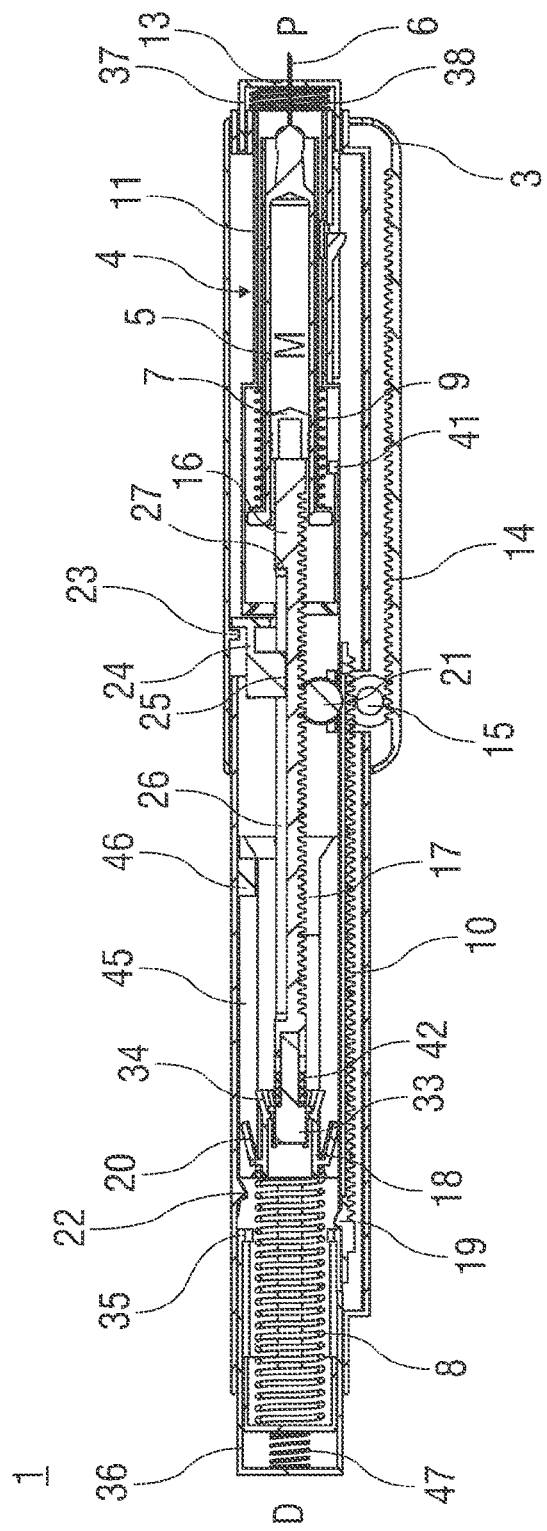
FIG. 11 is the auto-injector during needle insertion into an injection site.

The user depresses the trigger button 36 translating it in proximal direction P into the housing 2. As the trigger button 36 moves, the trigger button arms 35 contact the ramped outer latch arms 20 on the drive collar 18 deflecting them inwards out of engagement with the first ribs 22 allowing the drive collar 18 to move freely with respect to the housing 2 (see FIG. 10). The force from the drive spring 8 is transferred through the drive collar 18, to the plunger 16 and on to the stopper 7. An inward third rib 43 on the inner latch arms 34 is arranged to bear against the shoulder 44 on the distal head 33. The inner latch arms 34 are funnelled into a section 45 of the housing 2 with a reduced diameter preventing outward deflection of the inner latch arms 34. Grooves in the reduced diameter section 45 are arranged to allow translation of the outer latch arms 20. Friction opposing motion of the stopper 7 with respect to the syringe 5 is greater than the force of the retraction spring 9 and the needle insertion force and hence the syringe 5 is advanced and the needle 6 is inserted into the injection site. An insertion depth is controlled by the flange 31 contacting a fourth rib 41 on the housing 2 extending through an aperture the package housing 11 (see FIG. 11).

Figure 12:
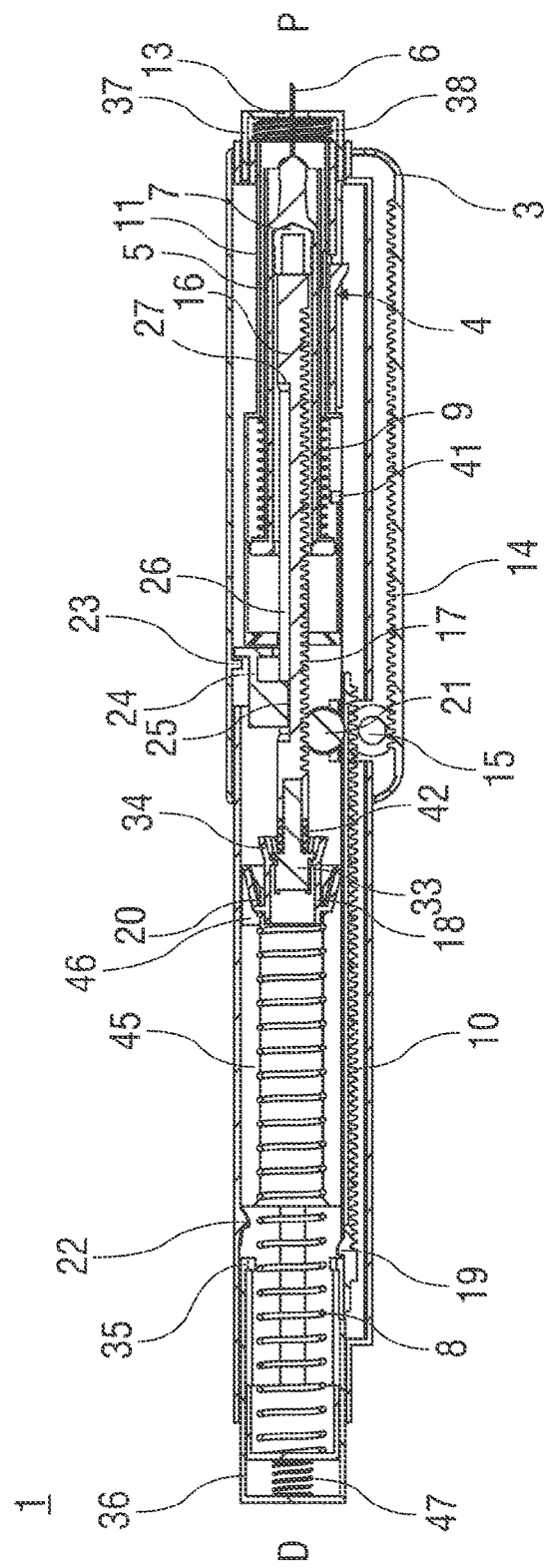
FIG. 12 is the auto-injector during injection.

Once the flange 31 contacts the fourth rib 41, the force from the drive spring 8 causes the plunger spring 42 to be compressed. Once compressed, the force on the stopper 7 is sufficient to overcome friction and emptying of the syringe contents (see FIG. 12).

If the auto-injector 1 is removed from the injection site at any point during the injection, the skin contact interlock 37 will be sprung forwards preventing access to the needle (not illustrated).

Towards the end of the dose (i.e. just before the stopper 7 bottoms out in the syringe 5) the outer latch arm 20 of the drive collar 18 contacts a viscous damper 46 arranged near a proximal end of the reduced diameter section 45. The load from the drive spring 8 is now shared between the stopper 7 and the viscous damper 46. This allows the plunger spring 42 to extend and complete the dose. The reaction force offered by the viscous damper 46 is speed dependent and hence an appropriate damping coefficient must be selected to ensure the full dose is delivered. The viscous damper 46 could be implemented with a visco-elastic foam material (see FIG. 12).

Figure 13:
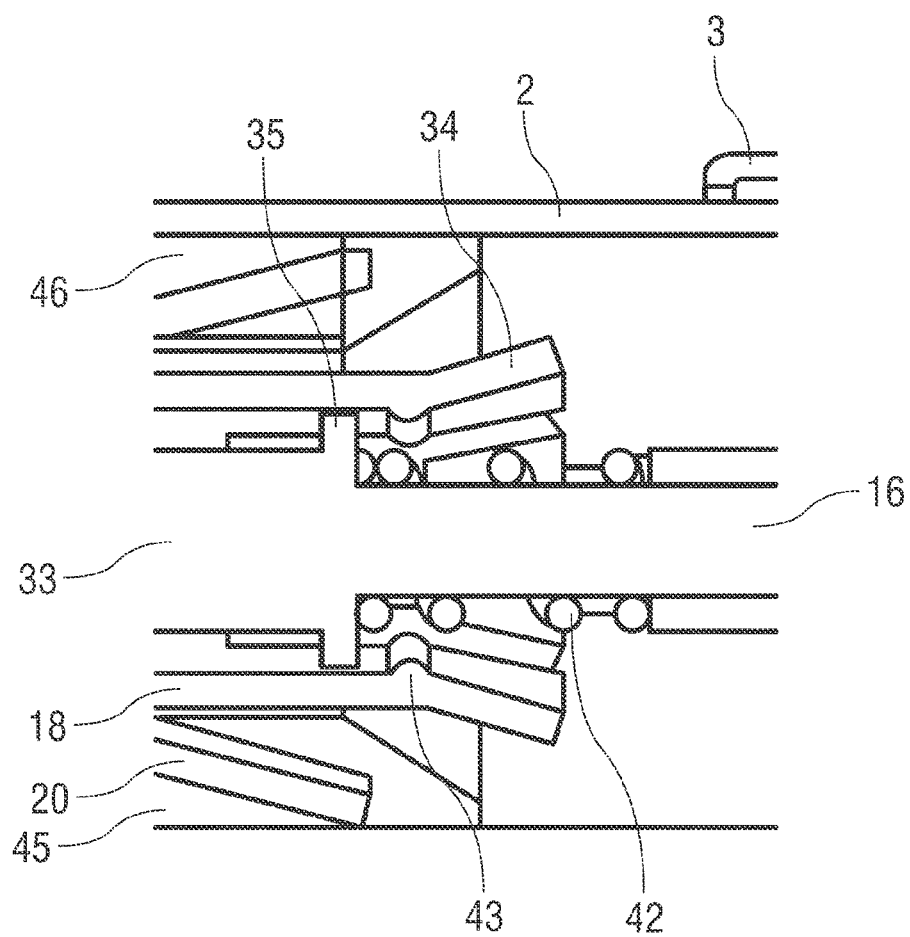
FIG. 13 is a detail view of a drive collar travelling past a plunger head.
Figure 14:
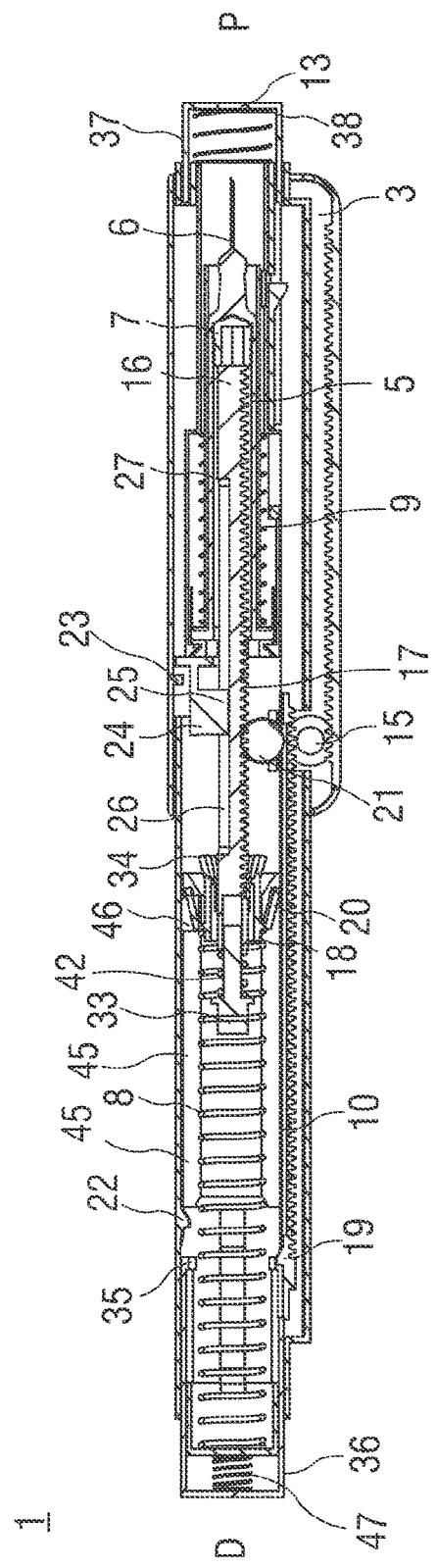
FIG. 14 is the auto-injector during needle retraction.

Once the viscous damper 46 is fully compressed, the position of the drive collar 18 is such that the inner latch arms 34 transmitting the force to the distal head 33 are no longer constrained in the reduced diameter section 45. The inner latch arms 34 are deflected radially outward enabling the distal head 33 to pass through the collar (see FIG. 13). Now the only force resolving the force of the retraction spring 9 is the friction of the needle 6 within the skin, which is in the range of 2 N and hence the retraction spring 9 withdraws the needle 6 from the skin. The syringe 5 is finally positioned in a retracted location within the package housing 11 of the packaged syringe 4 (see FIG. 14). This prevents user access to the needle 6 once removed from the re-usable auto-injector 1. Only when the sliding door 3 is fully opened is the syringe 5 locked in this retracted position. The injection is now complete.

The user then removes the auto-injector 1 from the skin and slides open the sliding door 3 in distal direction D to reveal the used packaged syringe 4. As the sliding door 3 is opened, the door rack gear 14 on the internal surface of the sliding door 3 meshes with the drive gear 15 which rotates with translation of the sliding door 3.

The drive gear 15 is in mesh with the plunger gear 21 which transmits a force to the plunger rack gear 17 on the plunger 16. Therefore, as the sliding door 3 is opened the plunger 16 is withdrawn from within the syringe 5. The drive gear 15 is also in mesh with the drive reset rack 10 and therefore as the sliding door 3 is moved the drive reset rack 10 moves in the proximal direction P. When the sliding door 3 is nearly fully open, the catch 19 on the drive reset rack 10 snaps proximally past the outer latch arms 20 (see FIG. 15).

In parallel, as the sliding door 3 approaches a fully open position, the boss 25 on the plunger shuttle 24 that is engaged in the longitudinal groove 26 on the plunger 16 reaches the end of free travel. Further movement of the plunger 16 is coupled to the plunger shuttle 24. The plunger shuttle 24 is frictionally coupled to the packaged syringe 4 by the ramps 28. Hence, the packaged syringe 4 is moved from the firing position to the loading bay 12. Once the packaged syringe 4 is positioned in the loading bay 12 the syringe shroud may contact the fourth rib 41 within the casework. The fourth rib 41 is arranged to define an end stop/limit of motion of the packaged syringe 4 in the distal direction D. As the packaged syringe 4 couples the fourth rib 41, the friction coupling of the ramps 28 on the plunger shuttle 24 is overcome and the syringe carrier sleeve 32 stops moving while the plunger shuttle 24 and plunger 16 continue to be withdrawn from the syringe 5 driven by the motion of the sliding door 3.

Once the sliding door 3 is fully opened, the packaged syringe 4 is returned to the loading bay 12, and the plunger 16 and plunger shuttle 24 are withdrawn sufficiently to enable removal of the used packaged syringe 4. The drive spring 8 is not compressed at this time.

A resilient feature beneath the packaged syringe 4 may be contacted by a proximal end of the drive reset rack 10 at the end of its travel in the proximal direction P as shown in FIG. 15. Thus the packaged syringe 4 may be lifted to facilitate removal.

The auto-injector 1 may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

The invention claimed is:

1. An auto-injector for delivering a liquid medicament, the auto-injector comprising an elongate housing having a longitudinal axis and a loading bay configured to receive a packaged syringe, wherein the loading bay is configured to be laterally accessible for inserting or removing the packaged syringe, wherein a sliding door is slidably arranged over the housing in a manner to reveal the loading bay when the sliding door is moved axially along the longitudinal axis to a distal position and to cover the loading bay when the sliding door is moved axially along the longitudinally axis to a proximal position, and where moving the door in a proximal direction causes compression of a drive spring, wherein the packaged syringe comprises a syringe with a hollow injection needle and a stopper for sealing the syringe and displacing the liquid medicament, wherein the drive spring is arranged in the housing for advancing the syringe and the needle in a proximal direction for needle insertion into an injection site and for injecting the medicament through the needle, wherein the sliding door exhibits a door rack gear in mesh with a drive gear which is in mesh with a drive reset rack such that the sliding door and the drive reset rack translate in opposite directions, and wherein the drive reset rack is arranged to compress the drive spring on translation in a distal direction.

2. The auto-injector according to claim 1, characterized in that a plunger is arranged for transferring load from the drive spring to the syringe and/or to the stopper, wherein the plunger comprises a plunger rack gear, wherein a plunger gear is in mesh with the drive gear and the plunger rack gear in such a manner that the plunger translates in the distal direction on translation of the sliding door in the distal direction whereas a sprag clutch allows translation of the plunger in the proximal direction without interference with the sliding door.

3. The auto-injector according to claim 1, characterized in that the drive spring is distally grounded in the housing and proximally bearing against a drive collar arranged to be engaged by the drive reset rack for compression of the drive spring and arranged to be latched to the housing when reaching a reset position during compression so as to prevent release of the drive spring.

4. The auto-injector according to claim 3, characterized in that a trigger button is arranged for de-latching the drive collar from the housing on depression in order to release the drive spring.

5. The auto-injector according to claim 4, characterized in that a skin contact interlock sleeve is slidably telescoped in the housing and biased in the proximal direction so as to protrude from the proximal end of the housing in a proximal position, wherein the skin contact interlock sleeve is arranged to be engaged with the trigger button in a manner to prevent depression of the trigger button when the skin contact interlock sleeve is in the proximal position and wherein the skin contact interlock sleeve is arranged to be deflected on depression in the distal direction in a manner to disengage from the trigger button thus allowing depression of the trigger button.

6. The auto-injector according to claim 3, characterized in that a plunger shuttle is slidably arranged in the housing, the plunger shuttle having a boss arranged to abut against a proximal stop on a plunger on translation of the plunger shuttle in the proximal direction, wherein a second rib on the sliding door is arranged to abut against the plunger shuttle on translation of the sliding door in the proximal direction, wherein the plunger shuttle is arranged to abut against the packaged syringe on translation in the proximal direction in such a manner that near the end of translation of the sliding door into the proximal position the sliding door translates the plunger shuttle, the plunger shuttle translates the packaged syringe into an actuate position and the plunger shuttle translates the plunger in such a manner that a distal head of the plunger passes through the drive collar and is latched to the drive collar for coupling the drive spring to the plunger.

7. The auto-injector according to claim 6, characterized in that the packaged syringe comprises a package housing, wherein the syringe is slidably arranged in the package housing, wherein at least one resilient snap arm in the package housing is arranged to prevent translation of the syringe relative to the package housing, wherein the plunger shuttle comprises at least one ramp arranged to deflect the at least one snap arm for releasing the syringe on further translation of the plunger shuttle when the packaged syringe is in the actuate position.

8. The auto-injector according to claim 6, characterized in that the distal head is telescoped with the plunger and biased against the plunger by a plunger spring.

9. The auto-injector according to claim 6, characterized in that the housing comprises a reduced diameter section arranged to prevent de-latching of the drive collar from the distal head of the plunger when the drive collar is between the reset position and a decoupling position where the stopper has at least nearly bottomed out in the syringe, such that the distal head de-latches from the drive collar under load of the drive spring in the decoupling position in a manner to allow it to translate in the distal direction independently from the drive collar.

10. The auto-injector according to claim 9, characterized in that a viscous damper is arranged for being contacted by the drive collar on translation just before the stopper bottoms out in the syringe, wherein the viscous damper is arranged to slow down the speed of the drive collar allowing the plunger spring to extend the stopper until it bottoms out, wherein the position of the viscous damper is selected relative to the reduced diameter section in a manner to allow de-latching of the distal head from the drive collar shortly before the viscous damper is fully compressed by the drive collar.

11. The auto-injector according to claim 9, characterized in that a retraction spring is arranged in the packaged syringe in a manner to be compressed on translation of the syringe for needle insertion and to retract the syringe and the needle on de-latching of the distal head from the drive collar.

12. The auto-injector according to claim 1, characterized in that the drive gear exhibits two different gearings with different numbers of gear teeth for respectively engaging the door rack gear and the drive reset rack in a manner to achieve reduced travel and increased force of the drive reset rack compared to the door rack gear.

* * * * *

UNITED STATES PATENT AND TRADEMARK OFFICE
CERTIFICATE OF CORRECTION

PATENT NO. : 9,061,103 B2
APPLICATION NO. : 13/994890
DATED : June 23, 2015
INVENTOR(S) : Thomas Kemp, Douglas Jennings and Matthew Ekman Page 1 of 1

It is certified that error appears in the above-identified patent and that said Letters Patent is hereby corrected as shown below:

In the specification

In column 1, line 8, delete "Dec. 12, 2011" and insert -- Dec. 21, 2011 --

Signed and Sealed this
Fifth Day of January, 2016

Michelle K. Lee
*Director of the United States Patent and Trademark Office*